(12) United States Patent
Oser et al.

(10) Patent No.: US 6,375,620 B1
(45) Date of Patent: Apr. 23, 2002

(54) PROCESS AND DEVICE FOR CARRYING OUT A VENOUS PLETHYSMOGRAPHY USING COMPRESSION

(75) Inventors: Daniel Oser, Woerthsee; Frank Christ, Gräfelfing, both of (DE)

(73) Assignee: Domed Medizintechnik GmbH, Graefelfing (DE)

( * ) Notice: Subject to any disclaimer, the term of this patent is extended or adjusted under 35 U.S.C. 154(b) by 0 days.

(21) Appl. No.: 09/051,329
(22) PCT Filed: Jun. 30, 1997
(86) PCT No.: PCT/EP97/03409
§ 371 Date: Jun. 15, 1998
§ 102(e) Date: Jun. 15, 1998
(87) PCT Pub. No.: WO98/06329
PCT Pub. Date: Feb. 19, 1998

(30) Foreign Application Priority Data

Aug. 9, 1996 (DE) .......................................... 196 32 263

(51) Int. Cl.$^7$ ................................ A61B 5/00; A61B 5/02
(52) U.S. Cl. ...................... 600/481; 128/903; 600/507
(58) Field of Search .................................. 600/481–488, 600/500–508, 490; 128/897–898, 900

(56) References Cited

U.S. PATENT DOCUMENTS 3,847,142 A * 11/1974 Williams, Jr. et al. ....... 600/481
4,718,426 A * 1/1988 Russell ......................... 600/481

* cited by examiner

*Primary Examiner*—Robert L. Nasser
*Assistant Examiner*—Michael Astorino
(74) *Attorney, Agent, or Firm*—Wood, Phillips, VanSanten, Clark & Mortimer

(57) ABSTRACT

Method and apparatus for venous compression plethysmography with a strain-gauge or by direct circumferential length measurement, the calibration of the measurement equipment being done automotively.

19 Claims, 4 Drawing Sheets

PROCESS AND DEVICE FOR CARRYING OUT A VENOUS PLETHYSMOGRAPHY USING COMPRESSION

BACKGROUND OF THE INVENTION

The present invention relates to a method and an apparatus for venous compression plethysmography.

Venous compression plethysmography is a procedure which has been known for some time now and which is used for determining microvascular parameters in the extremities, such as the venous capacity, the venous elasticity, the venous outflow rate, the arterial blood flow and the capillary filtration rate. In general, venous compression plethysmography allows qualitative and quantitative statements to be made concerning the state and function of the microvascular circulation in an extremity of a patient.

Venous compression plethysmography can be carried out in a very wide variety of ways, for example as water plethysmography, air plethysmography, impedance plethysmography, capacitance plethysmography, induction plethysmography or strain-gauge plethysmography. These procedures make use of different physical phenomena for determining the state of the blood vessels in a body part. The present invention relates to strain-gauge plethysmography and to compression plethysmography by means of direct induction-based measurement of circumferential change.

In strain-gauge plethysmography, an expandable strain-gauge is laid around the body part which is to be examined, for example an arm or a leg. The venous return of the blood is then obstructed in this body part using an inflatable cuff arranged nearer to the heart. The blood congestion leads to a change in the circumference of the body part in question, which in turn leads to expansion of the strain-gauge. From the expansion of the strain-gauge, which depends on the pressure applied to the cuff, it is possible to draw conclusions regarding characteristics or changes in the blood vessels. This evaluation of the expansion as a function of the induced congestion is based on known procedures.

In strain-gauge plethysmography today, it is normal to use a strain-gauge consisting of an expandable silicone tubing filled with mercury. In the event of expansion of the body part around which the strain-gauge is laid, the silicone tubing expands and deforms the mercury column located therein. As a result, the electrical resistance of the mercury column changes. This change in resistance is measured and from this it is then possible to draw conclusions regarding the expansion of the silicone tubing and, consequently, of the body part. This conclusion necessarily assumes knowledge of the relationship between the change in resistance and the strain-gauge expansion. Apparatuses for strain-gauge plethysmography must therefore be calibrated prior to their use. This calibration must be carried out virtually before each single examination of a body part, since the ratio of the resistance of the mercury column to the expansion of the strain-gauge depends on a large number of parameters, such as the ambient temperature and the patient's body temperature, the initial stress of the silicone tubing and the circumference of the body part examined.

The calibration is carried out by expanding the strain-gauge in a defined manner, while it is fastened in the examination position, and by measuring the change in resistance which occurs. In this case, several successive defined expansions of the strain-gauge are normally carried out, and the associated changes in resistance measured. A conversion factor is then calculated from this, assuming a linear relationship or other relationship of the measurement parameters. For calibration purposes, a calibration apparatus is arranged on the strain-gauge, and in conventional equipment this calibration apparatus generally consists of a knurled screw for expanding the strain-gauge. During calibration, the operator, for example a doctor or a nurse, then successively adjusts the length of the strain-gauge manually.

With this manual changing of the expansion, the operator is continuously exerting disturbing forces on the mostly very light measuring system, so that, for an exact measurement, it is necessary to wait for the relaxation of the system again and again. The relaxation times of the system can in these cases be very long and very different. An additional expansion of the silicone tubing, for example, can relax relatively quickly, whilst an impression in the tissue of the body part to be examined requires very much more time to return to the initial state. This leads to considerable time losses in the examination. Moreover, in the case of manual contact with the measurement device which bears on the body part, there is the risk of the strain-gauge being shifted on the patient's skin. This can lead to errors in the calibration and, thus, to inaccuracies in the evaluation of the measured values. A particular disadvantage is that it very much depends on the skill of the operator as to whether the measurement can be carried out quickly and reliably. The measurement thus loses some of its reliability as well as its reproducibility. For the measurement error caused by the operator to remain unchanged during a series of measurements, it would in fact be necessary for the same operator to carry out all the measurements. This is of course not really possible in prolonged series of tests and research projects.

SUMMARY OF THE INVENTION

The object of the invention is therefore to make available a method and an apparatus for strain-gauge plethysmography, which method is quick and easy to use but at the same time reliably provides accurate measured values.

According to one aspect of the invention there is provided a method for venous compression plethysmography, in which an extremity is surrounded by a cuff, whose internal diameter I can be varied, in such a way that an obstruction of the blood outflow can be generated in those veins of the extremity which are situated remote from the heart in isolation to the cuff, where a strain-gauge is arranged on the extremity in order to encircle the latter, at a point remote from the hear in relation to the cuff, in such a way that a tissue distension of the extremity, occurring as a result of an obstruction of the blood outflow, causes an expansion $\Delta D$ of the strain-gauge, where the expansion $\Delta D$ of the strain gauge, as a function of a measurement of the change $\Delta I$ of the internal diameter I of the cuff, is detected by determining the change $\Delta M$ of a measurement parameter M, and where the relationship between the strain-gauge expansion $\Delta D$ and the measurement parameter change $\Delta M$ is determined by calibration with the aid of a calibration apparatus connected to the strain-gauge, by determining at least one measurement parameter change $\Delta M_{12}$ for a defined expansion $\Delta D_{12}$, characterized in that the defined expansion $\Delta D$ for the calibration is generated by an adjustment mechanism in the calibration apparatus without an operator touching the strain-gauge or the calibration apparatus.

According to a further aspect of the invention, there is provided an apparatus for venous compression plethsymography with a cuff, whose internal diameter I can be varied, and which is suitable for encircling an extremity, with a measurement device arranged distally thereof, characterized in that the measurement device consists of a first area which is laid around the extremity and has an essentially low-expansion, dimensionally non-stable force transmission element which is guided round the circumference of an essentially band-like support belt, of a second area which is in operational communication with the two ends of the low-expansion, dimensionally non-stable force transmission element in such a way that a circumferential linear change of the extremity, by means of the low-expansion, dimensionally non-stable force transmission element, is detected by a measurement apparatus, where one end of the low-expansion, dimensionally non-stable force transmission element is in contact with the measurement apparatus, and the other end of the low-expansion, dimensionally non-stable force transmission element is secured on an adjustable bearing arrangement, or in that the measurement device consists of a first area which is laid around the extremity and has an essentially expandable, dimensionally non-stable force transmission element which is guided round the circumference of an essentially band-like support belt, of a second area which is in operational communication with the two ends of the expandable, dimensionally non-stable force transmission element in such a way that a circumferential linear change of the extremity, by means of the expandable, dimensionally non-stable force transmission element, is detected by a measurement apparatus, where one end of the expandable, dimensionally non-stable force transmission element is in contact with the measurement apparatus, and the other end of the expandable, dimensionally non-stable force transmission element is secured on an adjustable bearing arrangement.

In the context of the present invention, a method and an apparatus are made available for venous compression plethysmography using a strain-gauge, where the strain-gauge is calibrated without being touched by an operator. The calibration is preferably done automotively using an electric motor, a pneumatic mechanism or a spring mechanism, which motor or mechanism provides for the adjustment of a knurled screw or other advancing device, so that the desired defined expansion can be set. Use of a microprocessor for controlling the calibration device is particularly preferred. In this way, the calibration of the expansion measurement can be undertaken without direct contact between the operator and the strain-gauge or calibration device.

BRIEF DESCRIPTION OF THE DRAWINGS

The apparatus according to the invention and the method according to the invention are described below with reference to the figures, where.

DETAILED DESCRIPTION OF THE INVENTION

Figure 1:
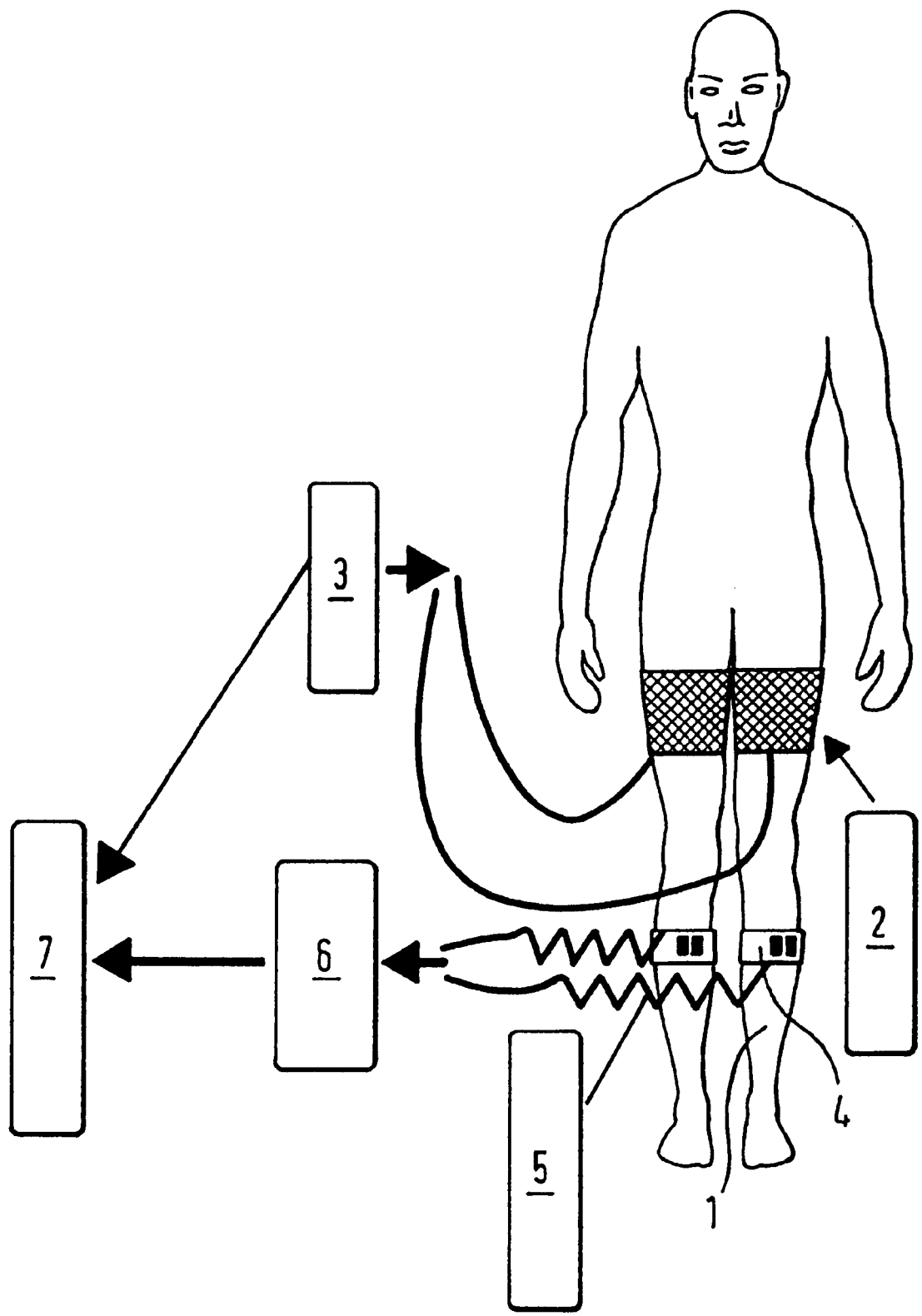
FIG. 1 shows the principle of strain-gauge plethysmography.

FIG. 1 shows an apparatus for venous compression plethysmography with a cuff 2, which encircles a body part 1, for example a leg, and whose internal diameter I can be varied using a pump 3. The apparatus further comprises a strain-gauge 4 which likewise encircles the body part 1. The strain-gauge 4 consists of a tubular flexible receiving material, preferably a silicone tubing, and of an expandable and electrically conducting material located therein, preferably mercury or a mercury-containing mixture. An electrical contact is in each case arranged at both ends of the strain-gauge 4. These contacts are connected via leads 5 to recording device 6, which is suitable for measuring the electrical resistance in the substance or a complementary variable such as the voltage drop or the current flow. The signals from the recording device 6 and the pump 3 are then fed to an evaluation unit 7, where the measurement results are evaluated as a function of a measure of the change in the internal diameter of the cuff 2, generally the pressure exerted on the cuff 2 by the pump 3.

Instead of the electrical resistance, any other desired measurement parameter M can be used as well, for example the number of interference lines of superimposing light beams, whose change ΔM is a measure of the expansion of the strain-gauge 4. The strain gauge can then be of a correspondingly different design, and does not therefore need to consist of a receiving material and of an electrically conducting substance arranged therein.

The strain-gauge 4 must be movable in the circumferential direction on the body part 1 in order to be able to expand along its entire length in the event of a change in the circumference of the body part 1. Otherwise, the strain-gauge 4 could remain stuck at one particular point of the body part 1, so that it would be locally overexpanded there, while not being expanded at all at other points. The consequence of this is unreliable measurements. In general, therefore, a sliding band is placed under the strain-gauge 4 to permit a movement of the strain-gauge 4 along the circumference of the body part 1. This can be achieved by the strain-gauge 4 sliding on the sliding band, or by the sliding band sliding on the skin, or by both effects. It is also conceivable, however, for the strain-gauge 4 itself to be designed, for example coated, such that it slides on the skin.

A calibration device is arranged on the strain gauge 4. In the context of the present invention, the calibration device is operated free of contact, that is to say without an operator touching it. This can be done, for example, with the aid of an electric motor or a pneumatic mechanism or else a spring mechanism in the calibration device. The calibration is preferably controlled by a microprocessor.

Figure 2:
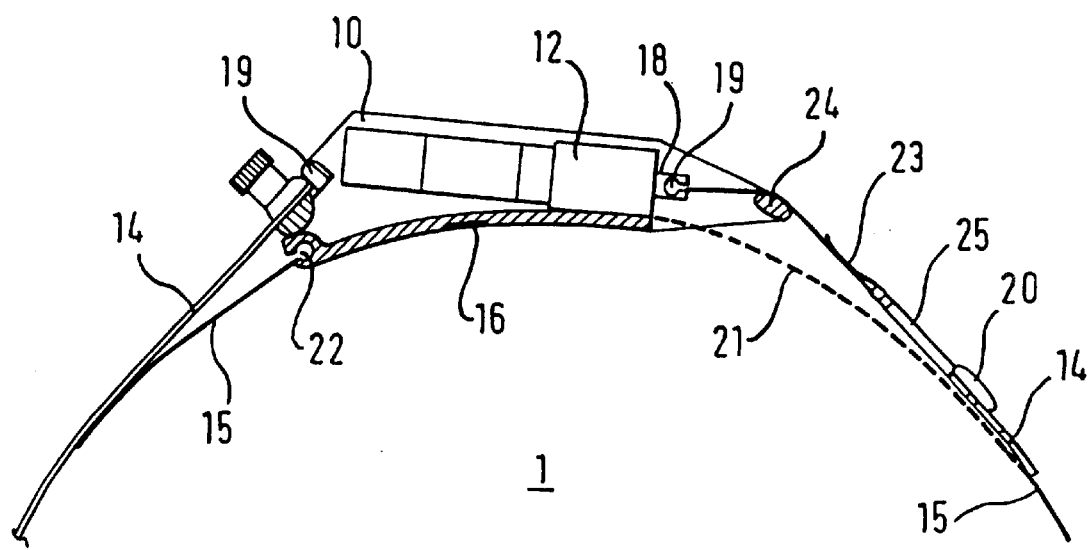
FIG. 2 shows the apparatus according to the invention for strain-gauge plethysmography.
Figure 2:
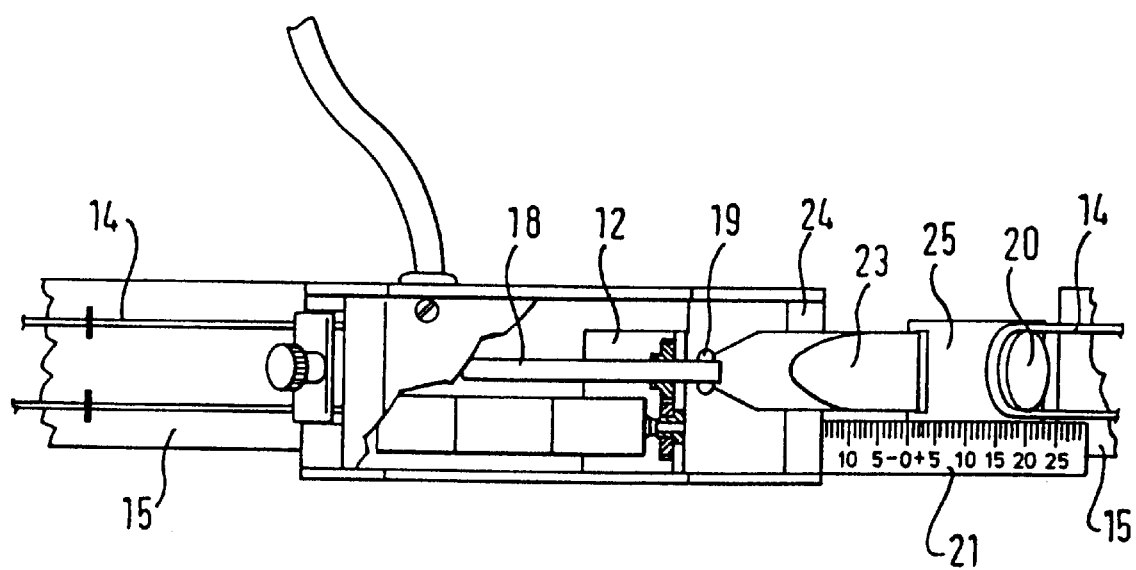

FIG. 2 shows a particularly preferred embodiment of the apparatus according to the invention. This apparatus has a calibration device 10 with at least the following elements: A linear drive 12 which is controlled without contact, for example electrically or pneumatically, with a push rod 18 which has a fastening point 19, and a tightening band 23 which consists of a first part which, at fastening point 19, is connected to the push rod 18 of the linear drive 12, and of a second part which is connected to the strain gauge 14 at a fastening point 20, the first part being guided as a loop through a bracket in the second part in such a way that the length of the tightening band 23 between the fastening points 19 and 20 can be varied. In this way, the measurement apparatus can be used on body parts of different circumference. The other end of the strain-gauge 14 is connected to the calibration device 10 at clamp device 13. The tightening band 23 can be guided via a deflector device 24 in order to ensure a correct travel. The end 25 of the tightening band 23 can be fixed on its opposite-running part, for example with a Velcro closure. The calibration device 10 moreover comprises a length measurement device 21 which can encircle the body part 1, but which can also consist only of a relatively small section. The length measurement device is arranged in such a way that the length of the strain-gauge 14 can be determined. The calibration device 10 preferably has a fastening point 22 for fastening a sliding band 15 encircling the body part 1, and, again preferably, it has a temperature sensor 16 for measurement of the surface temperature of the body part 1. The arrangement of a further temperature sensor (not shown here) for the ambient temperature is particularly preferred. If technically possible, a single temperature sensor can of course be used for determining the skin temperature and the ambient temperature. It is also possible for a single temperature sensor to measure a combined temperature of skin and ambient temperature if this temperature is suitable for correcting the measured values.

The apparatus shown in FIG. 1 is operated as follows, in accordance with the method according to the invention. A cuff 2 is placed around a body part 1 which is to be examined. This body part can be a relatively large extremity, such as a leg or an arm, but smaller extremities, such as fingers or toes, may also be examined. When correspondingly pressurized via the pump 3, this cuff 2 generates a blockage of the return flow of venous blood in the distally situated body part 1. A strain-gauge 4 is then arranged on the same body part, at a point more distant from the heart. When the body part 1 changes circumference as a result of the blood outflow obstruction which has been generated, the strain-gauge 4 also expands correspondingly. Thus, for example, the substance in the strain-gauge 4 changes its electrical resistance. This change in resistance is measured by a measuring unit 6 which is connected via lead 5 to both ends of the strain-gauge 4. At a defined pressure on the cuff 2, which is a measure of its internal diameter I or of the change $\Delta I$ in this internal diameter, in order to take the change $\Delta R$ in the resistance R of the substance and from this draw conclusions on an expansion $\Delta D$ of the strain-gauge 4, the apparatus must first be calibrated. The calibration is done by setting a defined expansion $\Delta D_{12}$ with the aid of the calibration device, driven for example by an electric motor, and by measuring the associated value of the resistance change $\Delta R_{12}$. This step can be repeated several times, depending on the requirements regarding measurement accuracy. The calibration is preferably carried out by evaluating two resistance changes $\Delta R_{12}$ and $\Delta R_{23}$ for two successivley defined expansions $\Delta D_{12}$ and $\Delta D_{23}$. However, a calibration by means of at least double determination of the resistance change $\Delta R_{12}$ for the same defined expansion $\Delta D_{12}$ is preferred, in which case the expansion, between two determinations of the resistance change, is taken back to the initial measure.

When using the apparatus according to FIG. 2, at the start of the measurement the strain-gauge 14 on sliding band 15 is placed around the body part 1. To do this, the first part of the tightening band 23 is guided through the bracket of the second part of the tightening band 23 and then fastened, for example using a Velcro closure, on the opposite-running part of the tightening band 23. The tightening band 23 is then set so that the expandable strain-gauge 14 surrounding the body part 1 has a defined predetermined length $L_0$. This is possible because the strain-gauge 14 does not encircle the entire body part 1, but is interrupted by the calibration device 10. The setting of a defined effective initial length $L_0$ of the strain-gauge 14 for the measurement is necessary because the force needed for a relative expansion $\Delta D$ depends on the absolute length or initial expansion of the strain-gauge 14. Effective length is here understood as the length of the strain-gauge 14 lying on the body part 1. The length gauge 21 which is arranged on the calibration device 10 and at least partially encloses the body part 1 permits determination of the effective length of the strain-gauge 14. By adjusting the length of the tightening band 23, the desired length $L_0$ of the strain gauge 14 can be set. With the aid of the length gauge 21, the unexpanded circumference of the body part 1 in the measurement plane can also be determined. If the length gauge 21 encloses the body part 1 completely, the circumference of the body part is measured directly; if the gauge 21 only partially encloses the body part 1, the desired size must be determined with the help of the known length, for example, of the sliding band 15.

During the measurement, the skin temperature of the body part 1 and the ambient temperature should be observed where possible. A change in the measured temperature by only a few degrees can already lead to an expansion of the strain-gauge 14, which leads to a significant measurement error. For this reason, a temperature sensor 16 for the surface temperature of the body part 1 is preferably provided. Since the measured temperature need not necessarily correspond with the temperature of the skin of the body part 1, a further temperature sensor can also be provided for the ambient temperature. A single measurement sensor can also be provided for both temperatures or for a combined temperature. According to the signals from the temperature sensors, the length of the strain-gauge 14 can then be readjusted, or the measurement otherwise corrected, or an error signal can be output which leads to the termination of the measurement.

The method according to the invention and the corresponding apparatus afford the requirements necessary for simply and reliably determining the absolute values of microvascular parameters and also of their periodic fluctuations.

It is a further object of the invention to make available an apparatus for compression plethysmography which effects a direct circumferential linear change and does not have the disadvantages of the prior art.

This object is achieved by the apparatus according to Patent claim 1.

In the context of the present invention, an apparatus is made available for venous compression plethysmography using a direct circumferential linear change, where the inductive displacement measuring device is calibrated without being touched by an operator. The calibration is preferably done automotively using an electric motor, a pneumatic mechanism or a spring mechanism, which motor or mechanism provides for the adjustment of a knurled screw or other advancing device, so that the desired defined expansion can be set. Use of a microprocessor for controlling the calibration device is particularly preferred. In this way, the calibration of the circumferential linear change can be undertaken without direct contact between the operator and the displacement measuring device or calibration device.

Figure 3:
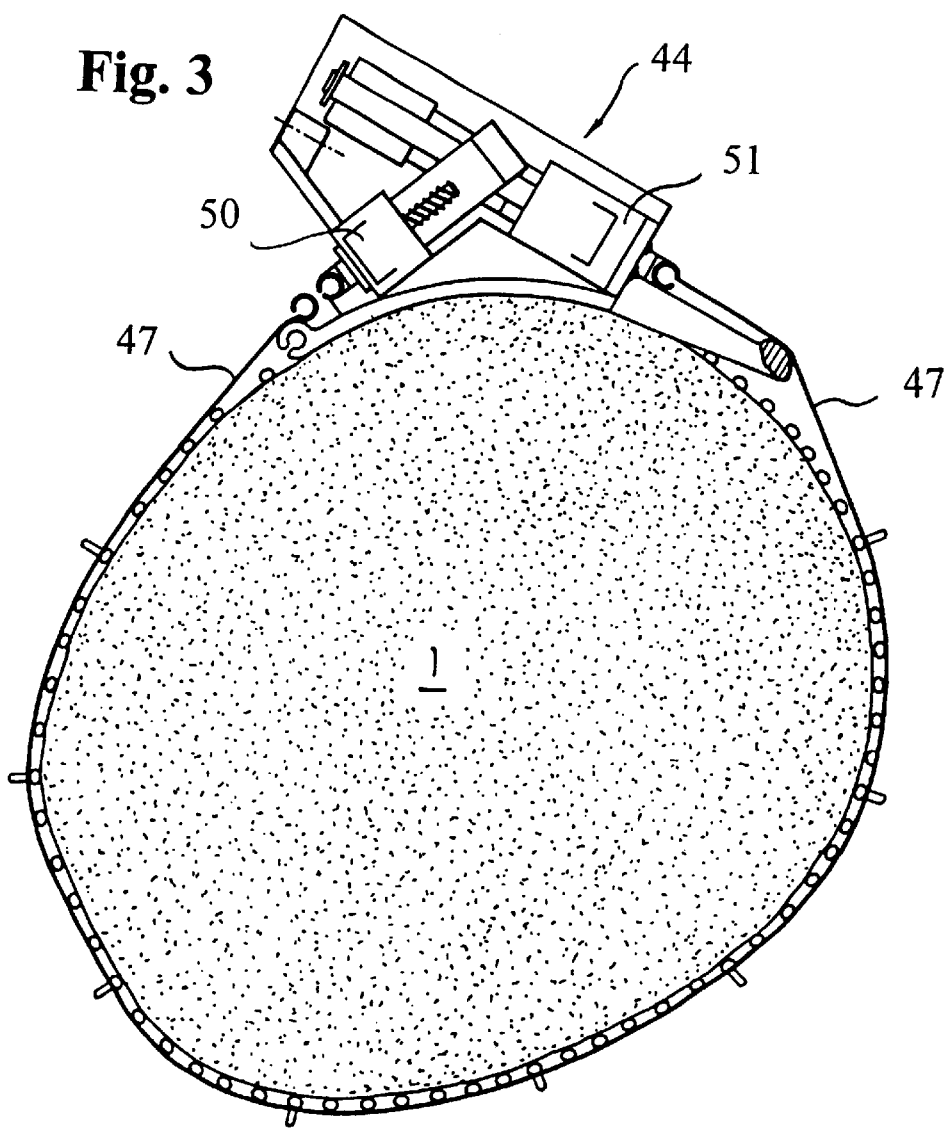
Figure 5:
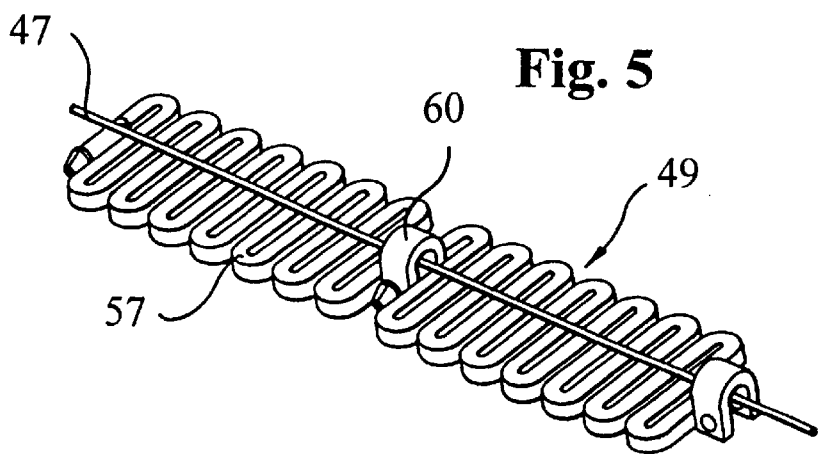
Figure 4:
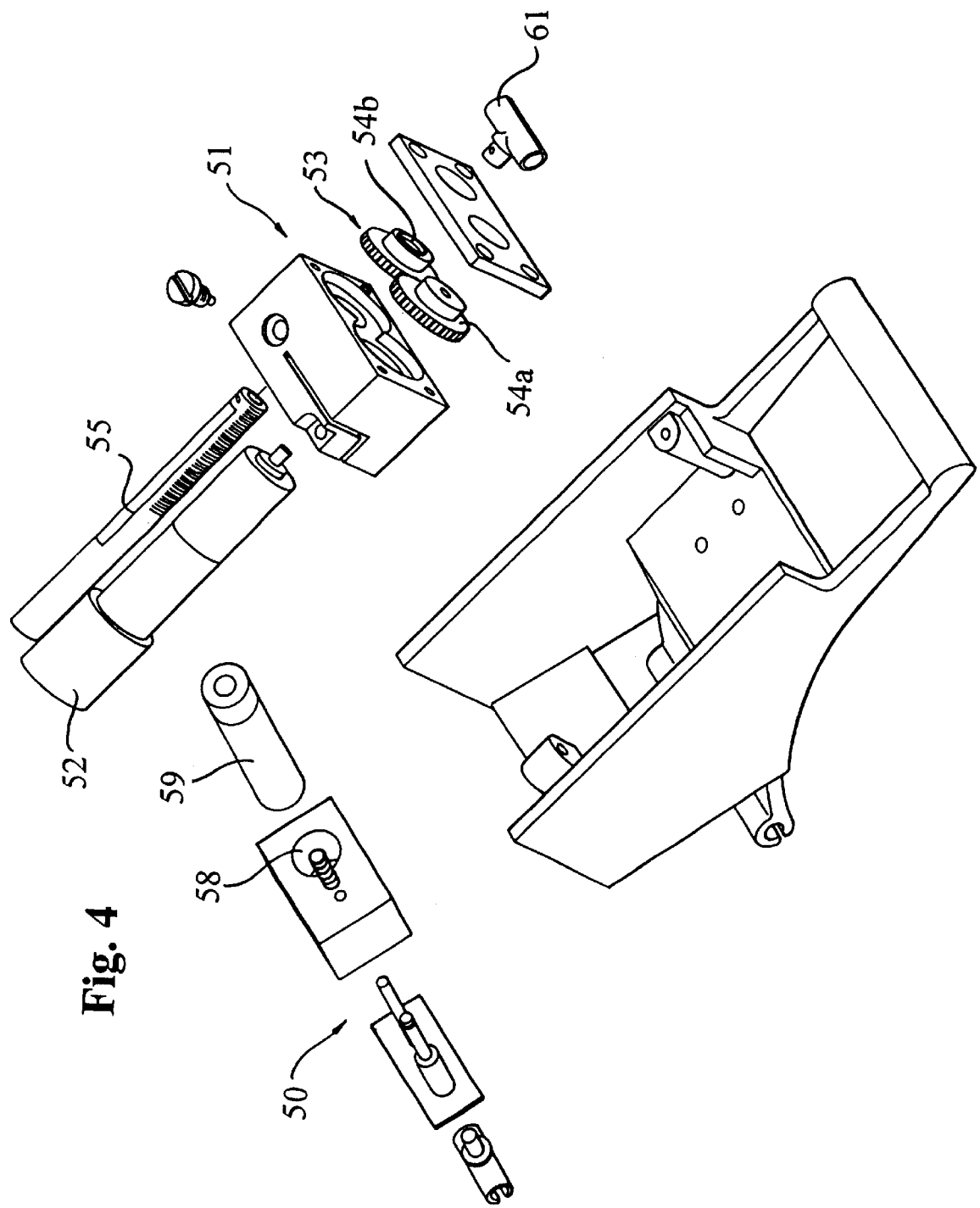

The apparatus according to the invention and the method according to the invention are described below with reference to the figures, where FIG. 3 shows the apparatus for compression plethysmography according to the invention, FIG. 4 shows an exploded view of the apparatus according to the invention, FIG. 5 shows a perspective view of the supporting belt according to the invention.

FIG. 1 shows an apparatus for venous compression plethysmography with a cuff 2, which encircles a body part 1, for example a leg, and whose internal diameter I can be varied using a pump 3. The apparatus further comprises a measurement device 4 which likewise encircles the body part 1. The measurement device 4 consists of a band-shaped support belt, an adjustable bearing arrangement 11, a displacement measuring device 10 and a low-expansion, dimensionally non-stable force transmission element 7.

The values obtained via the displacement measuring device are connected via leads 5 to recording device 6. The signals from the recording device 6 and the pump 3 are then fed to an evaluation unit 7, where the measurement results are evaluated as a function of a measure of the change in the internal diameter of the cuff 2, generally the pressure exerted on the cuff 2 by the pump 3.

A calibration device is arranged on the measurement device 4. The calibration device is operated free of contact, that is to say without an operator touching it. This can be done, for example, with the aid of an electric motor or a pneumatic mechanism or else a spring mechanism in the calibration device. The calibration is preferably controlled by a microprocessor.

FIG. 3 shows a particularly preferred embodiment of the apparatus according to the invention. This apparatus has an adjustable bearing arrangement with at least the following elements: An actuator 10 controlled without contact, for example electrically or pneumatically, with a push rod 13, a gear stage, which consists of two spur wheels, and a coupling piece 21, on which the low-expansion, dimensionally non-stable force transmission element can be coupled.

FIG. 4 shows an exploded view of the individual structural units of the measurement device 4 according to the invention. The displacement measuring device 10 of the apparatus according to the invention consists of a cylinder 19 which is moved in a bore 18. By means of the movement, an induction voltage is induced, so that the distance travelled is in relation to the induced voltage.

Another design of the displacement measuring device of the apparatus according to the invention is also possible, for example piezoelectronic sensors which can deliver a corresponding signal, or optic displacement measuring devices which can measure distances, for example by incremental transmitters.

Another embodiment integrates the bearing arrangement and the displacement measuring device in such a way that, for calibration, only one signal has to be called up, namely the induction voltage in relation to the spindle height. This can be done, for example, in a piezoelectronic actuator.

The bearing arrangement 11 according to the invention has an electric actuator 12 to which a gear stage 13 is connected downstream. The gear stage 13 has a spur wheel 14a on the front of the electric actuator 12 and a spur wheel 14b on the front of a spindle rod 15, the hub of the spur wheel 14b being of an open design, and the low-expansion, dimensionally non-stable force transmission element 30 being connected releasably to the spindle rod. The actuator 12 drives the gear stage 13, and the spindle rod 15 executes a linear movement through an internal thread in spur wheel 14b. This linear movement is able to tighten or loosen the low-expansion, dimensionally non-stable force transmission element by means of coupling piece 21, so that controlled readjustment of the force transmission element can take place.

The apparatus shown in FIG. 1 is operated as follows. A cuff 2 is placed around a body part 1 which is to be examined. This body part can be a relatively large extremity, such as a leg or an arm, but smaller extremities, such as fingers or toes, may also be examined. When correspondingly pressurized via the pump 3, this cuff 2 generates a blockage of the return flow of venous blood in the distally situated body part 1. A measurement device 4 is then arranged on the same body part, at a point more distant from the heart. When the body part 1 changes circumference as a result of the blood outflow obstruction which has been generated, the support belt is expanded, which results in an excursion of the force transmission element in the displacement measuring device, as a result of which a voltage is induced. This change in voltage is measured by a measuring unit 6 which is connected via lead 5 to both ends of the strain-gauge 4. At a defined pressure on the cuff 2, which is a measure of its internal diameter I or of the change $\Delta I$ in this internal diameter, in order to take the change $\Delta V$ in the displacement measuring device and from this draw conclusions on a linear change $\Delta L$ of the force transmission element, the apparatus must first be calibrated. The calibration is done by setting a defined expansion $\Delta L_{12}$ with the aid of the calibration device, driven for example by an electric motor, and by measuring the associated value of the resistance change $\Delta V_{12}$. This step can be repeated several times, depending on the requirements regarding measurement accuracy. The calibration is preferably carried out by evaluating two voltage changes $\Delta V_{12}$ and $\Delta V_{23}$ for two successively defined expansions $\Delta L_{12}$ and $\Delta L_{23}$. However, a calibration by means of at least double determination of the voltage change $\Delta V_{12}$ for the same defined expansion $\Delta L_{12}$ is preferred, in which case the expansion, between two determinations of the voltage change, is taken back to the initial measure.

When using the apparatus according to FIG. 4, at the start of the measurement the support belt is placed around the body part 1. The length of the support belt can be varied, as a function of the circumference of the extremity, by means of individual elements being connected in modular fashion to each other. This is preferably done by snap connections which ensure both a secure fit and reliable releasability. After the measurement device has been placed in the desired manner on the extremity, the calibration is performed.

FIG. 5 shows the band shaped support belt 9 according to the invention which serves as a bearing on the skin of the extremity 1 and is designed such that it affords a reliable fit on the surface of the skin, essentially by adhesion, so that it is possible to prevent the measurement device from slipping. The support belt 9 preferably has a meandering cross-section which extends in the longitudinal direction. By means of this meandering configuration, the support belt 9 can be expanded in the longitudinal direction upon tensile loading, and so carry along the guide devices 20 located on the top surface. The guiding of the force transmission elements 30 is thus at all times reliable and essentially free from friction. The support belt 9 moreover has modular individual elements which can be connected to one another by a releasable snap connection in such a way that the length of the support belt can be adjusted as desired, in order to take account of the conditions of different extremities.

For the safe and reliable guiding of the force transmission member 30 elements, the modular individual elements have devices which are preferably of circular design.

The low-expansion, dimensionally non-stable force transmission member 30 is preferably a yarn made of a polyester material which is further distinguished by a smooth and thus low-friction surface. Other materials are also possible for the force transmission member 30, for example polyamide yarns or carbon fibres.

The apparatus according to the invention affords the requirements necessary for simply and reliably determining the absolute values of microvascular parameters and also of their periodic fluctuations.

What is claimed is:

1. Method for venous compression plethysmography, in which an extremity is surrounded by a cuff, whose internal diameter can be varied in such a way that an obstruction of the blood outflow can be generated in those veins of the extremity which are situated remote from the heart in relation to the cuff, said method comprising:

arranging a strain-gauge on the extremity in order to encircle the latter at a point remote from the heart in relation to the cuff whereby a tissue distension of the extremity occurring as a result of an obstruction of the blood outflow causes an expansion of the strain-gauge, detecting the expansion of the strain-gauge as a function of a measurement of the change of the internal diameter of the cuff by determining the change of a measurement parameter, and determining a relationship between the strain-gauge expansion and the measurement parameter change by calibrating with a calibration apparatus connected to the strain-gauge, by determining at least one measurement parameter change for a defined expansion, wherein the defined expansion for the calibration is generated by a hands-free adjustment mechanism in the calibration apparatus, said adjustment mechanism adapted for hands-free operation without an operator touching the strain gauge or the calibration apparatus.

2. Method according to claim 1, characterized in that the receiving material is a silicone tubing.

3. Method according to claim 2, characterized in that the substance is expandable and electrically conducting.

4. Method according to claim 1, characterized in that the defined expansion for the calibration is generated with the aid of one of an electric motor a pneumatic mechanism, or spring mechanism in the calibration apparatus.

5. Method according to claim 1, characterized in that the calibration is controlled by a microprocessor.

6. Method according to claim 1, characterized in that the calibration is effected by evaluation of two measurement parameter changes for two successive defined expansions.

7. Method according to claim 1, characterized in that the calibration is effected by at least twice determining the measurement parameter change for the same defined expansion, in which case the expansion between two determinations of the measurement parameter change is taken back to the initial measure.

8. Method according to claim 1, characterized in that the substance is expandable and electrically conducting.

9. Apparatus for venous compression plethysmography with a cuff, whose internal diameter can be varied, and which is suitable for encircling a body part, with a strain-gauge which is suitable for encircling the body part, and with a calibration apparatus which is connected to the strain-gauge and permits a defined expansion of the gauge, characterized in that the calibration apparatus has an adjustment mechanism adapted to expand the gauge by the defined expansion, said adjustment mechanism adapted for hands-free operation.

10. Apparatus according to claim 9, wherein the strain-gauge consists of a receiving material and of an electrically conducting substance located therein, and has contacts for measuring the electrical resistance in the substance.

11. Apparatus according to claim 9, characterized in that the receiving material is a silicone tubing.

12. Apparatus according to claim 11, characterized in that the substance includes mercury.

13. Apparatus according to claim 9, characterized in that the calibration apparatus contains one of an electric motor and a pneumatic mechanism for generating the defined expansion.

14. Apparatus according to claim 9, characterized by a microprocessor for controlling the calibration.

15. Apparatus according to claim 9, characterized by said calibration apparatus having:

a contactlessly controlled linear drive with a push rod which has a fastening point, a tightening band which consists of a first part which, at one fastening point, is connected to the push rod of the linear drive, and of a second part connected to the strain-gauge at a second fastening point, the first part being guided as a loop through a bracket in the second part whereby the length of the tightening band between the fastening points can be varied, and a length measurement device adapted to encircle the body part thereon whereby the effective length of the strain-gauge and the circumference of the body part can be determined in a measurement plane.

16. Apparatus according to claim 9, characterized by a fastening point (22) for fastening a sliding band (15) encircling the body part (1).

17. Apparatus according to claim 9, characterized by a temperature sensor for measurement of at least one of the surface temperature and the ambient temperature of the body part.

18. Apparatus according to claim 9, characterized in that the substance includes mercury.

19. Method for venous compression plethysmography, in which an extremity is surrounded by a cuff, whose internal diameter can be varied in such a way that an obstruction of the blood outflow can be generated in those veins of the extremity which are situated remote from the heart in relation to the cuff, said method comprising:

arranging a strain-gauge on the extremity in order to encircle the latter at a point remote from the heart in relation to the cuff whereby a tissue distension of the extremity occurring as a result of an obstruction of the blood outflow causes an expansion of the strain-gauge, detecting the expansion of the strain-gauge as a function of a measurement of the change of the internal diameter of the cuff by determining the change of a measurement parameter, and determining a relationship between the strain-gauge expansion and the measurement parameter change by calibrating with a calibration apparatus connected to the strain-gauge, by determining at least one measurement parameter change for a defined expansion, wherein the defined expansion for the calibration is generated by a hands-free adjustment mechanism in the calibration apparatus, said adjustment mechanism adapted for hands-free operation without an operator touching the strain gauge or the calibration apparatus, wherein the electrical resistance in a substance is used as said measurement parameter, where the strain-gauge consists of a receiving material and of the substance located therein, and has contacts for measuring the electrical resistance in the substance.

* * * * *